United States Patent
Loutis et al.

(10) Patent No.: US 6,415,170 B1
(45) Date of Patent: Jul. 2, 2002

(54) BIOMEDICAL ELECTRODE AND METHOD FOR ITS MANUFACTURE

(75) Inventors: Nikolaus Loutis; Derek Wright, both of Borken; Paul Wiedenhaupt, Gummersbach, all of (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/214,878

(22) PCT Filed: Jul. 14, 1997

(86) PCT No.: PCT/US97/12124

§ 371 (c)(1),
(2), (4) Date: May 3, 1999

(87) PCT Pub. No.: WO98/02089

PCT Pub. Date: Jan. 22, 1998

(30) Foreign Application Priority Data

Dec. 9, 1996 (GB) .............................................. 9625533

(51) Int. Cl.$^7$ ................................................. A61B 5/04
(52) U.S. Cl. ........................ 600/391; 600/394; 600/397
(58) Field of Search ........................ 607/152; 29/592.1; 156/267; 600/372–392

(56) References Cited

U.S. PATENT DOCUMENTS

| | | | |
|---|---|---|---|
| 3,841,312 A | 10/1974 | Corasanti ............... | 128/2.06 E |
| 4,117,846 A | 10/1978 | Williams ............... | 128/303.13 |
| 4,282,878 A | 8/1981 | Novello ................ | 128/641 |
| 4,352,359 A | 10/1982 | Larimore et al. ........... | 128/640 |
| 4,441,500 A * | 4/1984 | Sessions et al. ............ | 600/392 |
| 4,640,289 A | 2/1987 | Craighead .................. | 128/639 |
| 4,727,881 A * | 3/1988 | Craighead et al. .......... | 128/641 |
| 4,938,219 A * | 7/1990 | Ishii et al. .................. | 128/641 |
| 5,215,087 A * | 6/1993 | Anderson et al. ........... | 128/640 |
| 5,406,945 A * | 4/1995 | Riazzi et al. ............... | 128/641 |
| 5,438,988 A * | 8/1995 | Duan et al. ................. | 600/391 |

FOREIGN PATENT DOCUMENTS

| | | | |
|---|---|---|---|
| EP | 0 142 372 | 5/1985 | ............ A61B/5/04 |
| EP | 0 276 661 B1 | 7/1993 | ......... A61B/5/0402 |
| EP | 0 360 496 B1 | 12/1994 | ......... A61B/5/0408 |
| WO | WO 93/00857 | 1/1993 | ............ A61B/5/04 |

* cited by examiner

Primary Examiner—Linda C. M. Dvorak
Assistant Examiner—David Ruddy
(74) Attorney, Agent, or Firm—John A. Burtis

(57) ABSTRACT

A biomedical electrode comprises a connector stud (1) anchored in a patch of adhesive-coated backing material (7) which is used to secure the electrode to the skin of a patient. The connector stud (1), which is located in a pierced opening in the backing material (7), has a head portion (2) to which an electrical lead of an electromedical monitoring/diagnostic system can be attached, and an electrode plate (3) which, when the biomedical electrode is in use, is placed in electrical communication with the skin of the patient. A strip of ionically-conductive adhesive (9) extends across the backing material and over the electrode plate (3) and a strip of scrim material (17) is located adjacent the adhesive coating on the backing material, underneath the adhesive strip (9). The two strips (9, 17) are displaced, relative to the electrode plate (3), towards a tab (13) which is used for removing the electrode from the skin of the patient.

29 Claims, 6 Drawing Sheets

BIOMEDICAL ELECTRODE AND METHOD FOR ITS MANUFACTURE

FIELD OF THE INVENTION

The present invention relates to biomedical electrodes, that is electrodes which can be attached to the skin of a patient to establish an electrical connection between the skin and an electromedical monitoring/diagnostic/therapeutic system. The invention relates more especially, but not exclusively, to ECG electrodes for use in a part of a system for monitoring and/or diagnosing cardiac function and is likewise applicable to electrodes for use in electroencephalograph (EEG) systems.

BACKGROUND OF THE INVENTION

ECG monitoring systems are well known and are used in a variety of health care situations. Such systems require the use of electrodes which are attached to the skin, at selected points of the body, to enable electrical signals (indicative of cardiac function) to be fed to an electrocardiograph. The electrodes, which are conventionally attached to the skin by an adhesive, are required to make good electrical contact with the skin and to be constructed to permit the easy attachment of electrical leads from the electrocardiograph. It is also desirable that the electrodes should be easy to remove from the protective liner material with which they are normally provided and from the skin of a patient, after use, without leaving any adhesive or other residues.

One known type of ECG electrode comprises a connector stud having a head portion to which electrical leads can be attached, and an electrode plate through which contact is made to the skin. The stud is located in a patch of backing material, with the electrode plate positioned on one side of the material and the head portion on the other. The side of the backing material on which the electrode plate is positioned is coated with an adhesive, enabling the ECG electrode to be securely attached to the skin and an electrical contact to be formed between the skin and the electrode plate. To improve the electrical connection between the skin and the electrode plate, the latter may, for example, be coated with a layer of an ionically-conductive paste, cream or gel, or covered with a layer of sponge material in which an ionically-conductive gel is embedded.

Connector studs which are formed in two parts, designed to snap together, are known. One part of the stud provides the electrode plate and the other part provides the head portion and, during the process of assembling the electrode, the two parts are located on opposite sides of the backing material and snapped together, thereby clamping the backing material between them. The connector stud is thus well anchored in the backing material so that the likelihood of it separating from the backing material when the electrode is in use is comparatively low. However, the two-part construction of the stud increases the complexity of the assembly process.

Biomedical electrodes with one-piece connector studs are also known. U.S. Pat. No. 4 352 359, for example, describes an electrode in which the connector stud is a one-piece stud, the head portion of which is located in a punched aperture in a patch of adhesive tape. The adhesive tape overlies the upper surface of the electrode stud and aids in holding the electrode securely to the skin of a patient. In another known electrode which employs a one-piece stud, the backing material is a comparatively thick foam material and an integral flange is provided in the stud at a distance from the electrode plate so that it will overlie the upper surface of the backing material. Additional shaping in the form of a smaller flange is provided on the stud between the flange and the electrode plate. The stud is located in a punched aperture in the backing material with the additional shaping on the stud thus being located within the aperture.

The use of one-piece connector studs reduces the number of components required to assemble a biomedical electrode but can increase the likelihood of the stud separating from the backing material, particularly when electrical leads are being attached to the stud. Alternatively, if the connector stud is shaped so that it is less likely to separate from the backing material, the insertion of the stud into the backing material during the assembly process can become more difficult.

U.S. Pat. No. 4 640 289 describes a biomedical electrode with a one-piece terminal member located in a punched aperture in a piece of adhesive, in which a retainer sheet is provided to prevent the terminal member separating from the remainder of the electrode. An automated method for producing the electrode is also described. The adhesive surface of the electrode is protected by a release liner and, to facilitate removal of the electrode from the release liner and, after use, from the skin of the patient, the electrode is provided with a tab formed in a margin of the adhesive tape.

U.S. Pat. Nos. 3,841,312 and 4,117,846 describe biomedical electrodes in which a separate ring or washer is employed to ensure that the connector stud is well anchored in a backing material.

SUMMARY OF THE INVENTION

The problem with which the present invention is concerned is that of enabling biomedical electrodes to be produced more simply and in a less costly manner without adversely affecting their reliability and convenience when in use.

The present invention provides a biomedical electrode comprising a backing material coated on one side with a pressure-sensitive adhesive and having a non-adhesive margin to facilitate the handling of the electrode; a connector stud located in the backing material, the stud having an electrode plate located on one side of the backing material for electrical connection to the skin of a patient and, on the other side of the backing material, a head portion to which an electrical connector can be attached; a strip of ionically-conductive adhesive extending, generally parallel to the non-adhesive margin, across the adhesive-coated side of the backing material and over the electrode plate of the stud; and a parallel strip of scrim material located at the interface of the ionically-conductive and pressure-sensitive adhesive; the strip of scrim material being displaced, relative to the electrode plate of the stud, towards the non-adhesive margin of the backing material and the edges of both strips nearest to the non-adhesive margin being positioned to one side of the electrode plate.

In one embodiment, the connector stud is one piece. In another embodiment, the connector stud comprises two pieces.

The invention further provides a biomedical electrode comprising a backing material coated on one side with a pressure-sensitive adhesive and having an adhesive-free margin to facilitate the handling of the electrode; a connector stud located in the backing material, the stud having an electrode plate located on one side of the backing material for electrical connection to the skin of the patient and, on the other side of the backing material, a head portion to which an electrical connector can be attached; and a strip of ionically-conductive adhesive extending across the adhesive-coated side of the backing material and over the electrode plate.

The present invention also provides a biomedical electrode comprising a backing material securable by an adhesive to the skin of a patient, and a connector stud located in a pierced opening in the backing material, the stud having an electrode plate located on one side of the backing material for electrical connection to the skin of the patient and, on the other side of the material, a head portion to which an electrical connector can be attached.

A method of manufacturing a biomedical electrode, comprising the steps of providing a connector stud comprising an electrode plate for electrical connection to the skin of a patient and a head portion; and inserting the connector stud into a pierced opening in a backing material, to locate the stud in the backing material with the electrode plate and the head portion on opposite sides of the material.

The present invention also provides a method of manufacturing a biomedical electrode, comprising the steps of forming an opening in a backing material; inserting a tubular member through the opening from one side of the backing material; providing a connector stud comprising an electrode plate for electrical connection to the skin of a patient, and a head portion; locating the stud, head portion first, in the end of the tubular member from the other side of the backing material.

By way of example only, embodiments of the invention will be described with reference to the accompanying drawings, in which:

EMBODIMENTS OF THE INVENTION

Figures 1, 2:
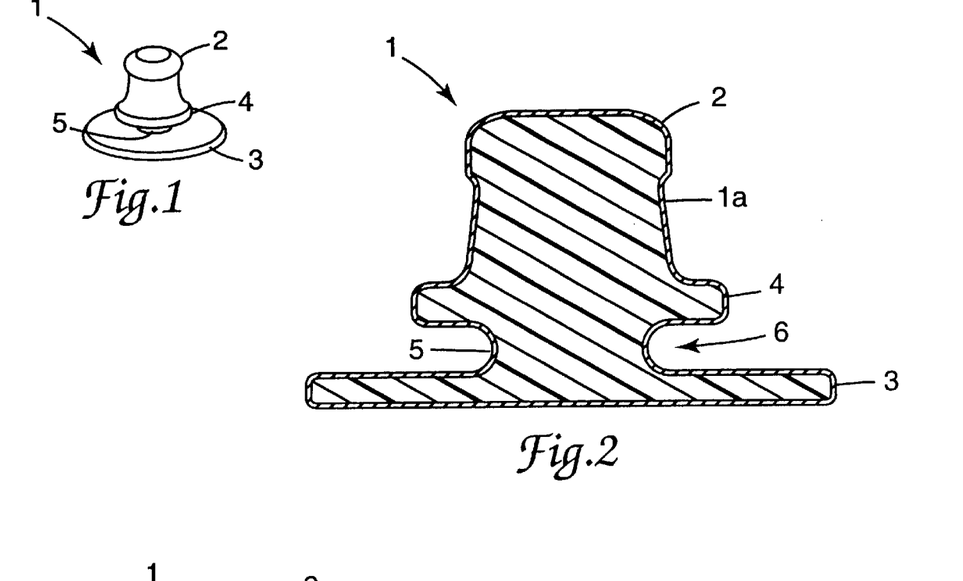
FIG. 1 is a perspective view of a connector stud for an ECG/EEG electrode, in accordance with the invention.
FIG. 2 shows a longitudinal cross-section on an enlarged scale through the stud of FIG. 1.

The connector stud 1 shown in FIGS. 1 and 2 is a one-piece moulded component comprising: a rounded head portion 2; a circular electrode plate 3 at the base of the stud; an outwardly projecting circular flange 4 which extends completely around the head portion 2 at the base of the latter; and, between the electrode plate 3 and the flange 4, a stem portion 5. The stem portion 5 is smooth, as can be seen from FIG. 2, so that the space 6 between the electrode plate and the flange is uninterrupted by any projections from the stem portion 5.

When in use in a biomedical electrode as described below, the bottom surface of the electrode plate 3 of the stud is placed in electrical communication with the skin of a patient and the stud 1 will then provide an electrical connection between the patient's skin and the head portion 2 of the stud, to which one lead of an electromedical monitoring/diagnostic system is connected. To enable the connector stud to be held in contact with the patient's skin, the stud is anchored in a piece of adhesive-coated backing material which is located, as will be described below, in the space 6 between the electrode plate 3 and the flange 4.

The stud 1 is preferably formed of a plastics material, for example a glass-filled copolymer of acrylonitrile, butadiene and styrene (ABS), with a coating 1a of an electrically-conductive material, for example silver/silver chloride. It may, however, be formed of any other material known to be suitable for the connector studs of biomedical electrodes, for example stainless steel or aluminium.

Typically, the diameter of the electrode plate 3 is about 10.15 mm; the maximum transverse dimension of the head portion is about 3.8 mm; the diameter of the flange 4 is about 6.0 mm; the diameter of the stem is about 2.45 mm; the height of the stud 1 is about 6.0 mm and the width of the space 6 is about 1.1 mm.

An ECG electrode incorporating the stud 1 is shown in FIGS. 3 to 6. The stud 1 is positioned in an opening (not visible in FIGS. 3 to 5) in the centre of a generally square patch of non-conductive backing material 7, with the backing material being held in the space 6 in the stud. In that way, the stud 1 is anchored in the backing material 7 with the electrode plate 3 located on one side of the material, and the flange 4 and head portion 2 located on the other. As will be described in greater detail below, the opening in the backing material (in which the stud 1 is located) is preferably a pierced opening but it could, alternatively, be a punched opening.

Figure 4:
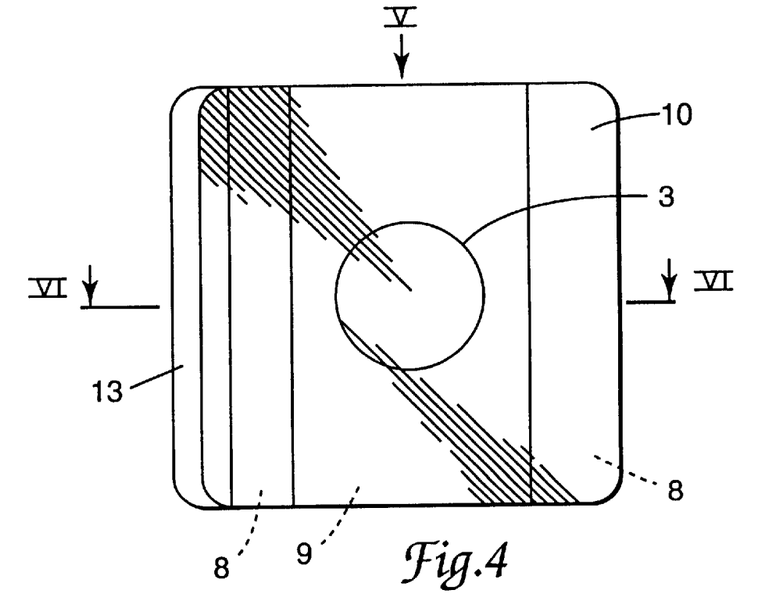
FIG. 4 is a view from below of the electrode shown in FIG. 3.
Figure 5:
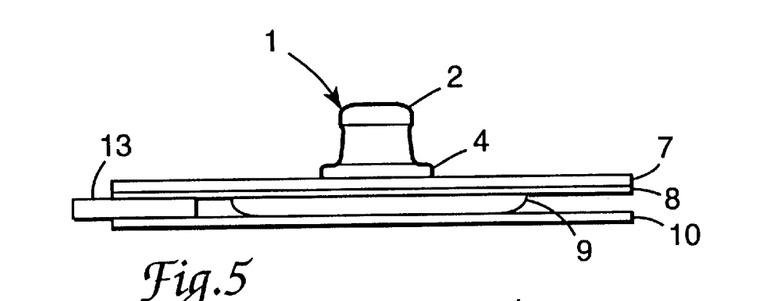
FIG. 5 is an enlarged, diagrammatic end view in the direction of the arrow V in FIG. 4.
Figure 6:
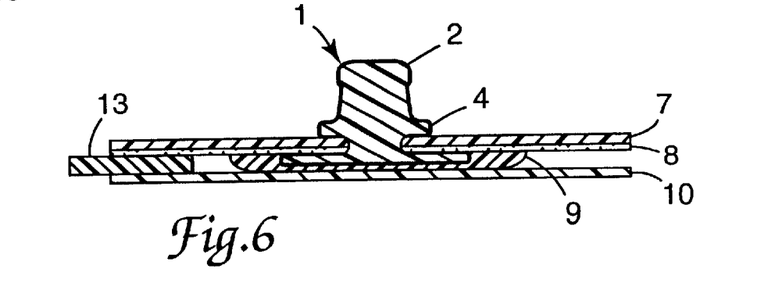
FIG. 6 shows an enlarged, diagrammatic, cross-section on the line VI—VI in FIG. 4.

The backing material 7 is typically a synthetic foam material, for example a 1 mm thick polyethylene foam film, about 34 mm×37 mm with rounded corners and, along one side, an extension 14 with a curved edge. The rear surface of the backing material 7 is provided with an adhesive coating comprising a pressure-sensitive adhesive 8 (which adhesive is preferably biocompatible with mammalian skin) over which is a strip 9 of an ionically-conductive adhesive which extends across the patch of backing material from one edge to the other, parallel to the side with the extension 14. The ionically-conductive adhesive covers the bottom surface of the electrode plate 3 of the stud and leaves two outer strips of the pressure-sensitive adhesive exposed. The central strip 9 of ionically-conductive adhesive is typically about 13.2 mm wide and, as shown in FIGS. 4 to 6, is displaced relative to the electrode plate 3 towards the extension 14, so that the edge 15 of the strip nearest to the extension 14 is located to one side of the electrode plate and the other edge 16 just touches the edge of the electrode plate.

To ensure good adhesion of the strip 9 of ionically-conductive adhesive to the backing material 7, a strip 17 of scrim material (not visible in FIG. 4) is located between the adhesive strip 9 and the pressure-sensitive adhesive 8 on the backing material. The scrim material is co-extensive with the adhesive strip 9 but, as shown in FIG. 6, is positioned on the other side of the electrode plate 3 (i.e. immediately adjacent the pressure-sensitive adhesive 8).

The adhesive coatings 8, 9 on the backing material are protected during storage until use by a removable liner 10 (shown as being transparent) which may be formed from any suitable material, for example a siliconized polyester film having a thickness of about 0.05 mm. A tab material 13 is located over the pressure-sensitive adhesive 8 on the extension 14 of the backing material 7, and remains in place to assist in removing the electrode from the liner 10 and also in removing the electrode, after use, from the skin of a patient. The tab material 13 may be formed from any suitable material, for example paper or polyester film and it may be coloured if desired.

The upper surface of the backing material 7 is covered by a label 18 of any suitable material, for example siliconized polyethylene, which may, if desired, be coloured or carry printed information. Adjacent the stud 1, the label 18 extends with the backing material into the gap 6 between the flange 4 and the electrode plate 3.

To ensure that the stud 1 will be well anchored in the backing material 7, the diameter of the flange 4 is preferably at least 1.3 (more preferably 1.5) times the maximum transverse dimension of the head portion 2. A process by which a connector stud 1 having a flange 4 of that size can be inserted into the backing material 7, and be well anchored, will be described below.

The pressure-sensitive adhesive 8 on the electrode backing material 7 can be any appropriate pressure-sensitive adhesive known to be suitable for use on biomedical electrodes. Suitable adhesives include acrylate ester adhesives, and more particularly acrylate ester copolymer adhesives. Such adhesives are generally described in U.S. Pat. Nos. 2,973,826; Re 24,906; Re 33,353; 3,389,827; 4,112,213; 4,310,509; 4,323,557; 4,732,808; 4,917,928; 4,917,929; and European Patent Publication 0,051,935.

The ionically-conductive adhesive 9 on the electrode backing material 7 can be any appropriate ionically-conductive adhesive known to be suitable for use on biomedical electrodes. Ionically-conductive adhesives useful in connection with biomedical electrodes are described in U.S. Pat. Nos. 4,524,087; 4,539,996; 4,848,353; 5,133,356; 5,225,473; 5,276,079; 5,338,490; 5,362,420; 5,385,679; and WO-A-95/20634 and WO-A-94/12585.

The strip of ionically-conductive adhesive 9 may be coated, either in a flood coating or in a pattern coating, onto the backing material 7 and then cured. If using a pattern coating, use of the process disclosed in PCT Patent Publication WO96/15715 can be used. Alternatively, as described below, the adhesive may be pre-cured and a strip of the pre-cured adhesive may be laminated to the backing material.

From the point of view of economy, the strips of ionically-conductive adhesive 9 and scrim material 17 are advantageously as narrow as possible consistent with reliability and with ensuring adequate electrical contact between the electrode plate and the skin of the patient. In the case of the electrode shown in FIGS. 3 to 6, that is achieved by arranging that the width of strips 9, 17 is such that the strips extend beyond the electrode plate 3 only on the side nearest the tab 13, 14 and then only by a very small amount (typically about 2 mm), just sufficient to ensure that the scrim material 17 can maintain the bond between the ionically-conductive adhesive 9 and the pressure-sensitive material 8 in the vicinity of the electrode plate 3 particularly when the electrode is removed either from the liner material 10 or, after use, from the patient's skin using the tab 13, 14.

Figure 7:
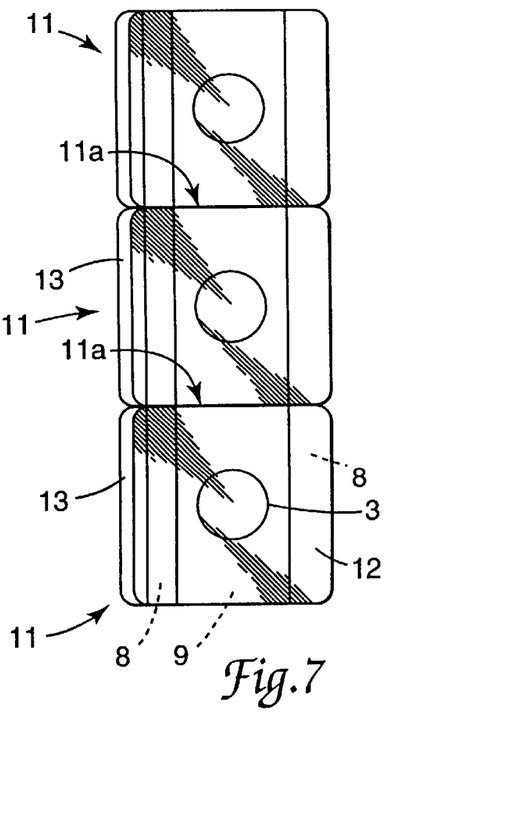
FIG. 7 is a view, similar to FIG. 4, of an alternative form of electrode.

In some cases. however, further economy can be achieved by reducing the width of the scrim material 17 still further and FIG. 7 is a view, similar to FIG. 4, illustrating how that can be done. In the electrode of FIG. 7, the scrim strip (the position of which is indicated by the shaded portion 19) has a width corresponding to the distance between the edge 15 of the conductive adhesive strip 9 and the nearest part of the electrode plate 3. A scrim strip which is slightly wider than illustrated in FIG. 7 could also be used and could be arranged to extend over, rather than under, the electrode plate 3 (i.e. adjacent the adhesive strip 9) provided that it is not so wide that it would impair the electrical connection between the adhesive strip 9 and the electrode plate 3.

The arrangement illustrated in FIG. 7 enables a reduced amount of scrim material to be used while ensuring that the ionically-conductive adhesive 9 remains well adhered to the backing material 7 and is not pulled away from the backing material when the electrode is removed either from the liner material 9 or, after use, from the patient's skin using the tab 13.

In the case of the electrode illustrated in FIGS. 3 to 6, the strip of scrim material is applied to the backing material 7 before the connector stud 1 is inserted. In the case of the electrode of FIG. 7, the scrim material can be applied to the backing material either before or after the connector stud 1 is inserted.

The non-conductive backing material 7 of the electrode can be any appropriate material, of any suitable thickness and shape (e.g. round. oval, rectangular). When the material is polyethylene foam, the most suitable thicknesses are within the range of from 0.75 to 1.5 mm. Other suitable materials, apart from the polyethylene foam described above include polyester non-woven materials, cellulose rayon non-woven materials, and polyethylene vinyl acetate films. When backing material is used which has a different thickness from the backing material 7 of FIGS. 3 to 6, the distance between the base 3 and the flange 4 of the connector stud 1 should be increased or decreased accordingly.

A process for producing electrodes as shown in FIGS. 3 to 6 will now be described with reference to FIG. 8. The process preferably comprises the following steps:

(i) A continuous strip of electrode backing material 19, laminated with label material 22 on one side and coated with a pressure-sensitive adhesive on the other side, is fed through a laminating station 20 in which a continuous strip of scrim material is 26 is laminated to the adhesive, in a location corresponding to the intended location of the scrim in the finished electrode. The backing material 19 fed to the station 20 also carries a narrow strip of tab material along one edge in a location corresponding to the tab material 13 in the finished electrode.

(ii) The backing material 19 is then fed to a stud insertion station 21, described in greater detail below, in which spaced connector studs are anchored in the scrim material.

(iii) The backing material 19 is then fed to a laminating station 23 in which a strip 24 of pre-cured ionically-conductive adhesive laminated to the liner material 25 for the finished product is applied over the scrim material and the line of connector studs.

(iv) The final laminated assembly, comprising backing material, scrim, connector studs, adhesives, tab material and product liner is then fed to a final cutting station 29, in which it is cut into individual electrodes.

The waste material is then removed, as indicated at 30.

The process described above can, if required, be carried out in such a way that two, or more, rows of electrodes are produced simultaneously across the width of the backing material 19.

The manner in which the connector studs are inserted into the backing material in the station 21 of FIG. 8 will now be described with reference to FIGS. 9 and 10. The backing material 19, with the strip of scrim material, passes over a piercing head 31 comprising a piercing tool 32 surrounded by a tubular sleeve 33. The adhesive-coated side of the backing material is uppermost as seen in FIG. 9 (i.e. it is the side remote from the piercing head 31). In steps (a) and (b), the piercing tool 32 is pushed through the backing material 19 and scrim. In step (c), the sleeve 33 is pushed through the pierced opening 34 in the backing material and holds it open while the piercing tool is withdrawn.

Subsequently, in steps (d) to (g), a connector stud 35 is placed (head portion first) into the end of the tubular sleeve 33 and is held in place, with the flange 4 of the stud engaging the end of the sleeve, as the latter is withdrawn through the opening 34. The stud is then released, in step (h) when it has reached the position in which the edges of the pierced opening are located in the space 6 (FIGS. 1 and 2) between the electrode plate 3 and the flange 4 of the stud. The backing material then passes to the station 23 of FIG. 8.

To prevent the connector studs 35 slipping too far into the tubular sleeve 33, the flange 4 of each stud should have a diameter greater than that of the sleeve. To enable the backing material 19 to lie flat around the stem 5 of each stud, the stem 5 should have as small a diameter as possible, preferably not more than 0.75 times that of the flange 4.

Figure 9:
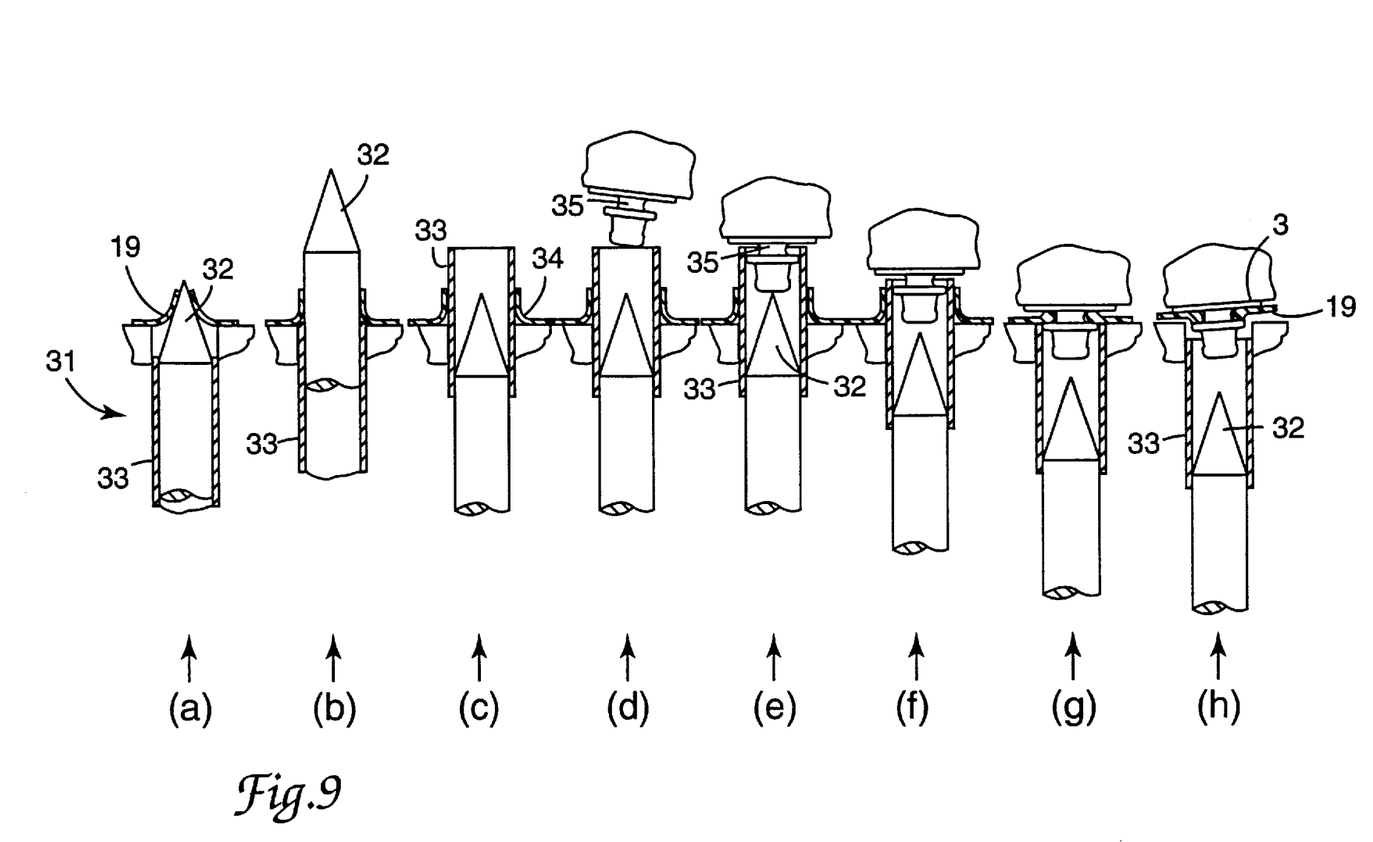
FIG. 9 illustrates, schematically, the insertion of connector studs into backing material in the process illustrated in FIG. 8.
Figure 10:
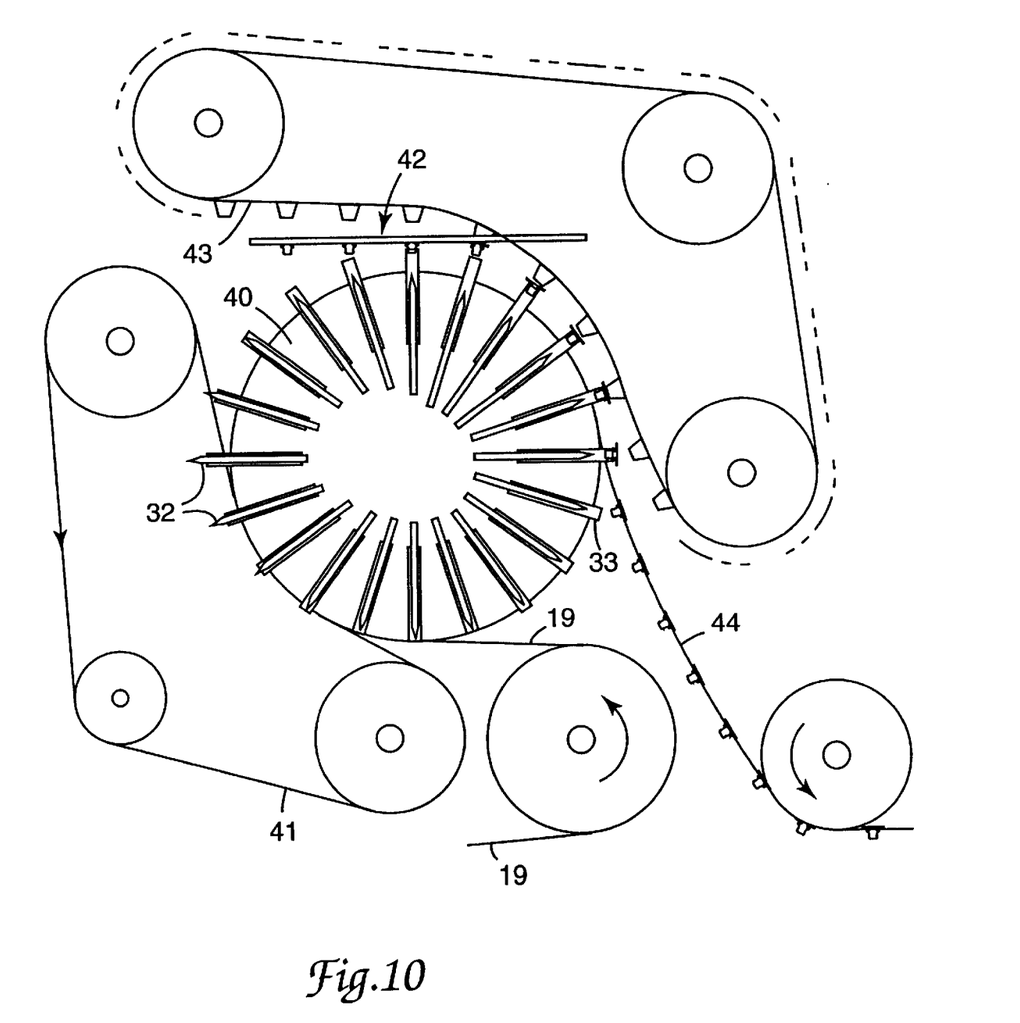
FIG. 10 illustrates apparatus for carrying out the process illustrated in FIG. 9.

Advantageously, the process illustrated in FIG. 9 is carried out continuously in the manner illustrated in FIG. 10. The backing material 19 with scrim passes over a continuously-driven insertion wheel 40 containing a plurality of radially-located piercing tools 32 and surrounding tubular sleeves 33. The piercing tools and sleeves 32, 33 are cam driven so that they each move uniformly in and out of the insertion wheel 40 in the manner illustrated in FIG. 9. The backing material 19 is initially held against the insertion wheel 40 by a first belt 41 while the pierced openings are being formed. Connector studs 1 to be placed on the ends of the sleeves 33 are then fed into position at 42 and held in place by a second belt 43 as the sleeves are withdrawn to locate the studs in the backing material 19 which is then removed as indicated at 44.

A pre-cured conductive adhesive for use in step (iii) of the process described above with reference to FIG. 8 can be prepared according to the following procedure. A precursor is prepared, having the following formulation (by weight): 18.61% acrylic acid; 0.05% 2,2-dimethoxy-2-phenyl acetophenone; 0.09% 4-(2-hydroxyethoxy) phenyl-(2-hydroxy-2-methylpropyl)ketone; 0.04% methylene bis (acrylamine); 41.39% glycerine; 21.35% deionized water; 0.09% guar gum; 16.53% NaOH (50% sol); 1.85% potassium chloride. The precursor can be prepared in the following manner: A kettle equipped with overhead stirrer and a cooling jacket is charged with the acrylic acid, 2,2-demethoxy-2-phenyl acetophenone, 4-(2-hydroxyethoxy) phenyl-(2-hydroxy-2-methylpropyl)ketone, methylene bis (acrylamide), glycerin, guar gum, and a proportion of the deionized water. To the well stirred solution is charged the 50% aqueous NaOH portionwise maintaining the batch temperature below 38° C. The hydroxide line is rinsed with deionized water and stirred. and the potassium chloride is then added as a 25% aqueous solution (preferably warmed to a temperature of about 80–90° F. (26 to 32° C.)) to yield a coater-ready precursor. The precursor is coated onto a siliconized polyester liner at 0.25 mm thick, overlaminated with a siliconized polyester liner, and passed through a curing chamber consisting of banks of fluorescent "black" lights, exposing the material to an intensity of 1.0 mW/sqcm and a total dose of 315 mJ/sqcm. Following removal of one of the polyester liners, the cured conductive adhesive so prepared is ready for use together with the final product liner in the laminating station 23 of FIG. 8.

To facilitate the handling of the cured adhesive and, if necessary, enable it to be transported from the location in which it is cured, a scrim material may be located on the liner material onto which the adhesive precursor is coated. Following curing, the scrim material will be embedded substantially in the middle of the adhesive layer.

A tubular sleeve, similar to the sleeve 33 of FIG. 9, can also be used when it is required to insert a stud of the type shown in FIGS. 1 and 2 into a punched (rather than pierced) hole in electrode backing material 7 and will facilitate the location of the stud in the hole, despite the comparatively large diameter of the flange 4 of the stud 1. When the stud is in position in the backing material, the comparatively large diameter of the flange 4 again ensures that the stud is well anchored in the backing material 7.

It will be appreciated that, although a continuous process as illustrated in FIGS. 9 and 10 is preferred in that it enables a fast production rate to be achieved (and the cost of producing electrodes to be reduced), it is not essential since the same process could be carried out intermittently.

Figure 3:
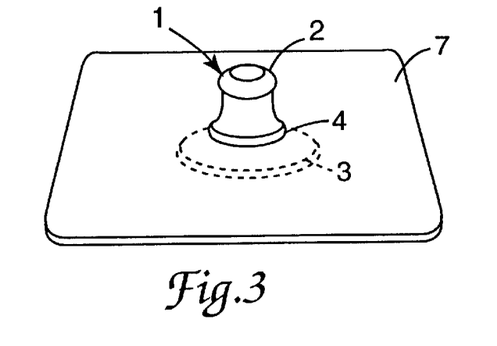
FIG. 3 is a perspective view, from above, of an ECG electrode incorporating the stud of FIGS. 1 and 2.

It will also be appreciated that the process could be used to produce electrodes having a different form from that shown in FIG. 3. For example, the overall shape of the connector studs 1 could be varied, as could the shape of the patches 7 of backing material. In addition, individual features of the process could be applied to the production of other forms of electrodes. For example, the step 23 (FIG. 8) of laminating a strip of pre-cured conductive adhesive with liner material to the backing material could be used in the production of many other types of biomedical electrodes, including electrodes which do not incorporate a connector stud. More specifically, strips of precured conductive adhesive could be used in biomedical electrodes of the type which comprise a patch of an ionically-conductive material which is secured directly to the skin and to which an electrical lead of an electromedical monitoring/ diagnostic/ therapeutic system can be attached. In that case, a strip of pre-cured adhesive could be laminated across the rear surface of the patch of ionically-conductive material.

Figure 8:
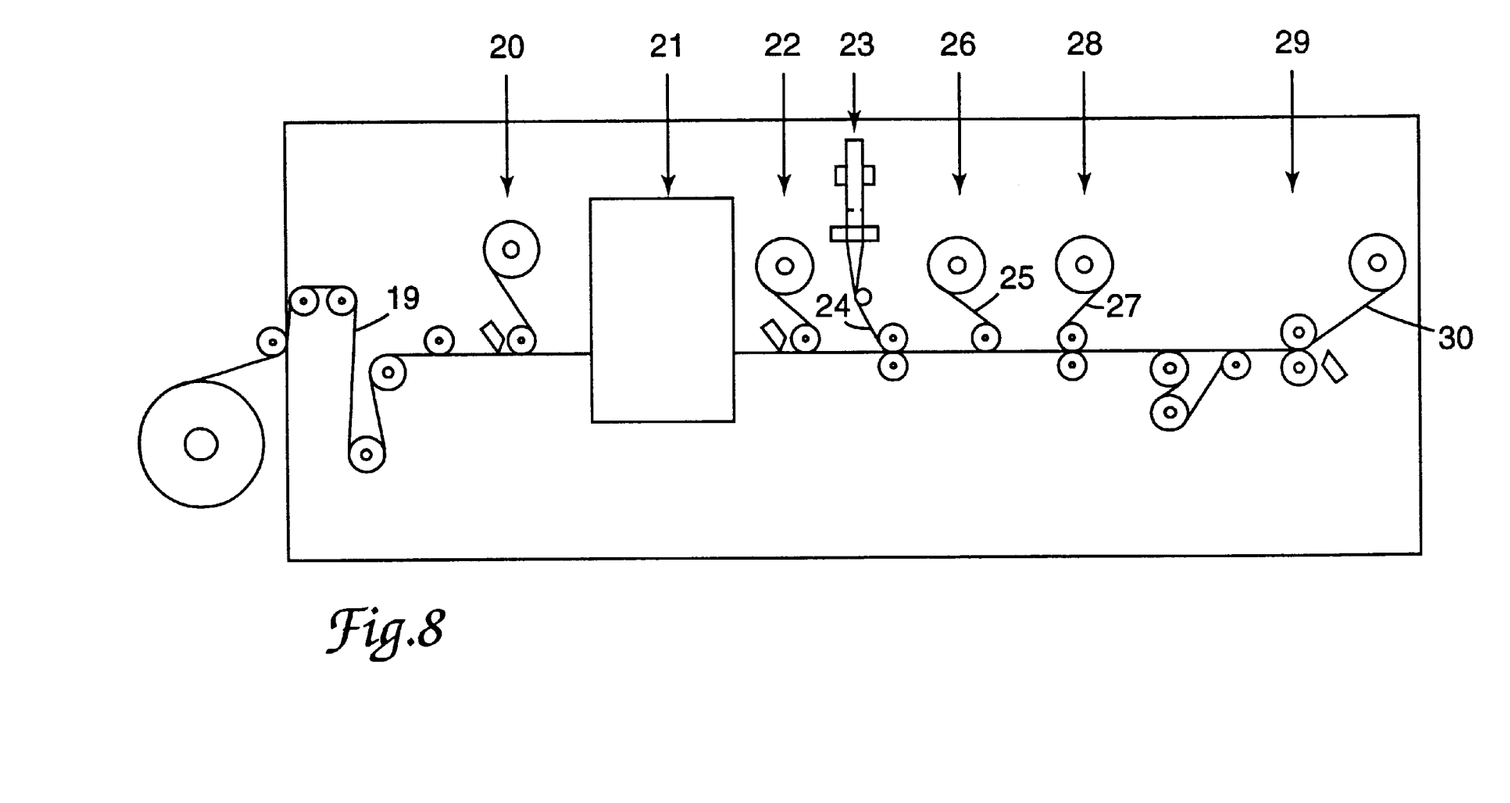
FIG. 8 illustrates, schematically, a process for the production of electrodes as shown in FIGS. 3 to 6.

A process similar to that illustrated in FIG. 8 could be used to produce electrodes of the type illustrated in FIG. 7. Alternatively, the process could be modified so that the scrim material is applied to the backing material after the connector studs have been inserted, but before the ionically-conductive adhesive is applied.

As a further alternative, the backing material 19 supplied to the laminating station 20 can be strip coated with the pressure-sensitive adhesive so that it has an adhesive-free margin along the side at which the tab 14 will be located in the final product. In that case, the material for the tab 13 is omitted but the label material on the other side may be distinctively marked (e.g. coloured) along that margin. The remainder of the process remains unchanged and the finished electrode will be the same as that shown in either FIG. 4 or FIG. 7 except that there will be no tab material 13 and the tab will, instead, be formed simply by the adhesive-free margin of the backing material with the label material on the upper surface of the electrode. In that way, further economies can be achieved because the material for the tab 13 is not required and less adhesive is used. The strip coating of the pressure-sensitive adhesive can be applied to a full width of backing material which is then slit into suitable widths for the process of FIG. 8. Advantageously, the width of backing material used in the process of FIG. 8 allows two electrodes to be formed side-by-side, in which case there would be an adhesive-free margin along each edge (typically about 5.0 mm wide) with a band of pressure-sensitive adhesive (about 60.5 mm wide between. In that case the full width of backing material would be strip coated with several parallel pressure-sensitive adhesive bands, each 60.5 mm wide, separated by adhesive free bands having a width of 10 mm. with 5.0 mm wide adhesive-free margins along each edge of the material. The full-width material would then be slit longitudinally at the mid-point of each adhesive free band. The full-width backing material could, if desired, be laminated with full-width label material which could carry tab-identifying printed stripes in locations corresponding to the adhesive-free bands on the backing material. Advantageously, the tab-identifying stripes are slightly wider than the adhesive-free bands (typically 12.0 mm wide).

Figure 11:
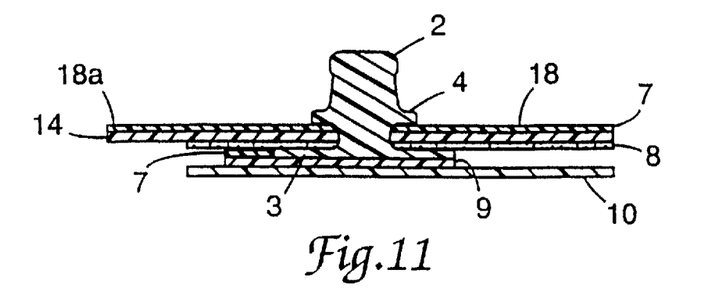
FIG. 11 is a view, similar to FIG. 6 of yet another form of electrode.

An electrode produced according to the method just described is illustrated in FIG. 11. The electrode is generally similar to that shown in FIG. 7 in that the width of the scrim material 17 is such that it extends only between the edge 15 of the adhesive strip 9 and the nearest part of the electrode plate 3. Corresponding parts of the electrode carry the same references as in FIG. 7. The tab portion 14 of the backing material 7 is free of adhesive and the overlying region 18a of the electrode label 18 is coloured to enable the tab to be readily identified.

Strip coating of adhesive material as used to produce the electrode shown in FIG. 11 is well known and need not be described in detail here. The use of strip coating in the production of biomedical electrodes is described, for example, in WO96/15715.

Figure 12:
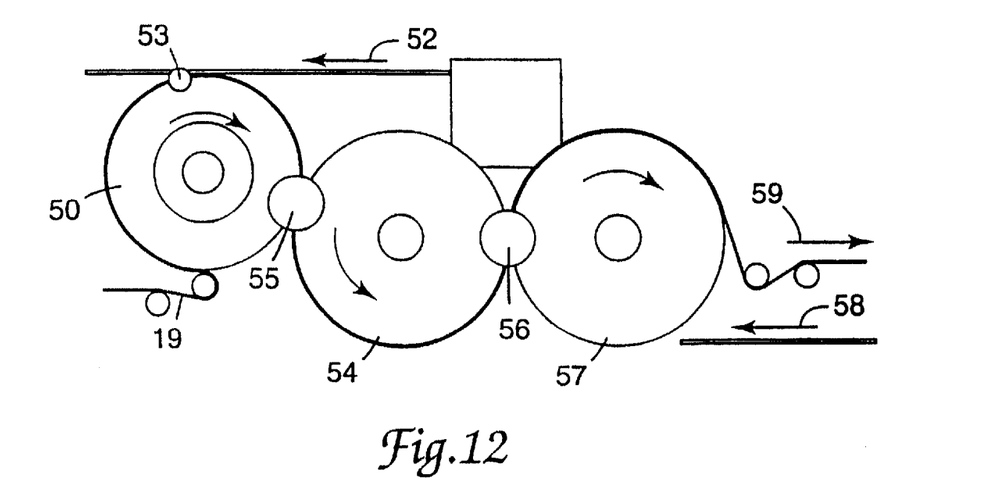
FIG. 12 illustrates apparatus for carrying out the process of an alternative embodiment.

An alternative embodiment to the electrode shown in FIG. 11 is an electrode comprising two pieces for the connector stud 1, a stud piece and an eyelet piece. It is known to those skilled in the art that a connector is more typically comprised of these two pieces, such as those stud/eyelet connectors used in the manufacture of 3M Red Dot™ biomedical electrodes by Minnesota Mining and Manufacturing Company (3M) of St. Paul, Minn. USA. Any of the stud/eyelet materials used in these commercial electrodes can be used in the process of the present invention. Manufacturing of a two-piece connector stud involves some alteration to the equipment shown in FIG. 10. FIG. 12 shows the apparatus useful for forming an electrode of the present invention that contains a two-piece connector stud.

A wheel 50 is the same as the wheel 40 shown in FIG. 10. Into backing material 19 moving along wheel 50, studs coming from direction 52 are inserted at junction 53 by the method described above for the single piece connector stud 1. The backing material 19, with studs therein, then passes to the wheel 54 at location 55 where the studs 52 are positioned ready to receive the eyelets at junction 56, fed in on wheel 57 from a line feeder from direction 58. The eyelets are pushed onto the studs at junction 56 between wheels 54 and 57. The backing material 19 is trapped between the studs and the eyelets and proceeds in assembled form along wheel 57 in direction 59.

Suitably-shaped and sized electrodes of the general type shown in FIGS. 3 to 6, 7 and 11, and described in FIG. 12 can be also used in association with EEG systems. Likewise, biomedical electrodes of the present invention can be connected electrically and mechanically to electrosurgical generators or cardiac stimulation devices to provide dispersive electrode connection or cardiac stimulation electrode connection, respectively. Electrosurgical generators are commonly available and known to those skilled in the art, such as devices marketed by Birtcher Medical Systems. Inc. Of Irvine, Calif. USA; Aspen Surgical Systems, Inc. Of Utica, N.Y. USA; and Valleylab, Inc. Of Boulder, Colo. USA. Cardiac stimulation devices for cardioversion, external pacing, and defibrillation are commonly available and known to those skilled in the art, such as devices marketed by Hewlett-Packard Corporation of McMinnville, Oreg. USA, Zoll Medical Corporation of Newton, Mass. USA and Physiocontrol Corporation of Redmond, Wash. USA.

Embodiments of the invention have been described. The claims follow.

What is claimed is:

1. A biomedical electrode comprising:
    (a) a backing material coated on a first side with a pressure-sensitive adhesive and having a non-adhesive margin to facilitate the handling of the electrode;
    (b) a connector stud located in the backing material, the stud having an electrode plate located on the first side of the backing material for electrical connection to the skin of a patient and, on a second side of the backing material, a head portion to which an electrical connector can be attached;
    (c) a strip of ionically-conductive adhesive extending, generally parallel to the non-adhesive margin, across the adhesive-coated first side of the backing material from edge to edge and over the electrode plate of the stud; and
    (d) a parallel strip of scrim material located at the interface of the ionically-conductive and pressure-sensitive adhesive, the strip of scrim material being displaced, relative to the electrode plate of the stud, towards the non-adhesive margin of the backing material, and the edges of both strips nearest to the non-adhesive margin being positioned to one side of the electrode plate.

2. biomedical electrode as claimed in claim 1, in which the edges of the strips of scrim material and ionically-conductive material nearest to the non-adhesive margin of the backing material are substantially contiguous.

3. A method of manufacturing a biomedical electrode, comprising:
    providing a connector stud comprising an electrode plate for electrical connection to the skin of a patient and a head portion;
    inserting the connector stud into a pierced opening in a backing material, to locate the stud in the backing material with the electrode plate and the head portion on opposite sides of the material; and
    providing a strip of scrim material located to one side of the center of the electrode plate of the stud on a first side of the backing material.

4. A method as claimed in claim 3, including the step of holding the pierced opening in an open condition while the stud is being inserted.

5. A method of manufacturing a biomedical electrode, comprising:
    forming an opening in a backing material;
    inserting a tubular member through the opening from one side of the backing material;
    providing a connector stud comprising an electrode plate for electrical connection to the skin of a patient, and a head portion;

locating the stud, head portion first, in the end of the tubular member from the other side of the backing material; and providing a strip of scrim material located to one side of the center of the electrode plate of the stud on a first side of the backing material.

6. A method as claimed in claim 5, in which the opening is a punched opening.

7. A biomedical electrode comprising:

a backing material coated on a first side with a pressure-sensitive adhesive and having a non-adhesive margin to facilitate the handling of the electrode;

a connector stud located in the backing material, the stud having an electrode plate located on the first side of the backing material for electrical connection to the skin of a patient and, on a second side of the backing material, a head portion to which an electrical connector can be attached;

a strip of ionically-conductive adhesive extending, generally parallel to the non-adhesive margin, across the adhesive-coated first side of the backing material and over the electrode plate of the stud, wherein the strip of ionically-conductive material is displaced, relative to the electrode plate of the stud, towards the non-adhesive margin of the backing material; and a parallel strip of scrim material located at the interface of the ionically-conductive and pressure-sensitive adhesive, the strip of scrim material being displaced, relative to the electrode plate of the stud, towards the non-adhesive margin of the backing material, and the edges of both strips nearest to the non-adhesive margin being positioned to one side of the electrode plate.

8. A biomedical electrode as claimed in claim 7, in which the edges of the strips of scrim material and ionically-conductive material nearest to the non-adhesive margin of the backing material are substantially contiguous.

9. A biomedical electrode as claimed in claim 7, in which the strip of scrim material is located to one side of the center of the electrode plate of the stud.

10. A biomedical electrode as claimed in claim 9, in which the strip of scrim material is located to one side of the electrode plate of the stud.

11. A biomedical electrode as claimed in claim 7, in which the strip of scrim material extends between the pressure-sensitive adhesive and the electrode plate of the stud.

12. A biomedical electrode as claimed in claim 11, in which the width of the strip of ionically-conductive adhesive is such that the adhesive covers the electrode plate of the stud but does not extend substantially beyond the electrode plate at the edge remote from the non-adhesive margin of the backing material.

13. A biomedical electrode as claimed in claim 12, in which the strips of adhesive and scrim material are substantially co-extensive.

14. A biomedical electrode as claimed in claim 13, in which the backing material is substantially rectangular in shape and has the non-adhesive margin along one side, the strips of scrim material and ionically-conductive adhesive extending across the backing material substantially parallel to the non-adhesive margin.

15. A biomedical electrode as claimed in claim 14, in which the scrim material is laminated to the pressure-sensitive adhesive on the backing material.

16. A biomedical electrode as claimed in claim 15, in which the ionically-conductive adhesive is in the form of a pre-cured strip which is laminated to the scrim and backing materials and to the electrode plate.

17. A biomedical electrode as claimed in claim 16, in which the connector stud is a one-piece stud and is located in a pierced hole in the backing material.

18. A biomedical electrode as claimed in claim 17, in which the adhesive-carrying side of the electrode is covered by a removable liner.

19. A biomedical electrode comprising:

a backing material coated on a first side with a pressure-sensitive adhesive and having a non-adhesive margin to facilitate the handling of the electrode;

a connector stud located in the backing material, the stud having an electrode plate located on the first side of the backing material for electrical connection to the skin of a patient and, on a second side of the backing material, a head portion to which an electrical connector can be attached;

a strip of ionically-conductive -adhesive-extending, generally parallel to the non-adhesive margin, across the adhesive-coated first side of the backing material and over the electrode plate of the stud; and a parallel strip of scrim material located at the interface of the ionically-conductive and pressure-sensitive adhesive, wherein the strip of scrim material is displaced, relative to the electrode plate of the stud, towards the non-adhesive margin of the backing material, wherein the edges of both strips nearest to the non-adhesive margin are positioned to one side of the electrode plate, and further wherein the strip of scrim material is located to one side of the center of the electrode plate of the stud.

20. A biomedical electrode as claimed in claim 19, in which the edges of the strips of scrim material and ionically-conductive material nearest to the non-adhesive margin of the backing material are substantially contiguous.

21. A biomedical electrode as claimed in claim 19, in which the strip of scrim material is located to one side of the electrode plate of the stud.

22. A biomedical electrode comprising:

a backing material coated on a first side with a pressure-sensitive adhesive and having a non-adhesive margin to facilitate the handling of the electrode;

a connector stud located in the backing material, the stud having an electrode plate located on the first side of the backing material for electrical connection to the skin of a patient and, on a second side of the backing material, a head portion to which an electrical connector can be attached;

a strip of ionically-conductive adhesive extending, generally parallel to the non-adhesive margin, across the adhesive-coated first side of the backing material and over the electrode plate of the stud; and a parallel strip of scrim material located at the interface of the ionically-conductive and pressure-sensitive adhesive, wherein the strip of scrim material is displaced, relative to the electrode plate of the stud, towards the non-adhesive margin of the backing material, wherein the edges of both strips nearest to the non-adhesive margin being positioned to one side of the electrode plate, and further wherein the strip of scrim material extends between the pressure-sensitive adhesive and the electrode plate of the stud.

23. A biomedical electrode as claimed in claim 22, in which the width of the strip of ionically-conductive adhesive is such that the adhesive covers the electrode plate of the stud but does not extend substantially beyond the electrode plate at the edge remote from the non-adhesive margin of the backing material.

24. A biomedical electrode as claimed in claim 23, in which the strips of adhesive and scrim material are substantially co-extensive.

25. A biomedical electrode as claimed in claim 24, in which the backing material is substantially rectangular in shape and has the non-adhesive margin along one side, the strips of scrim material and ionically-conductive adhesive extending across the backing material substantially parallel to the non-adhesive margin.

26. A biomedical electrode as claimed in claim 25, in which the scrim material is laminated to the pressure-sensitive adhesive on the backing material.

27. A biomedical electrode as claimed in claim 26, in which the ionically-conductive adhesive is in the form of a pre-cured strip which is laminated to the scrim and backing materials and to the electrode plate.

28. A biomedical electrode as claimed in claim 27, in which the connector stud is a one-piece stud and is located in a pierced hole in the backing material.

29. A biomedical electrode as claimed in claim 28, in which the adhesive-carrying side of the electrode is covered by a removable liner.

* * * * *

UNITED STATES PATENT AND TRADEMARK OFFICE
CERTIFICATE OF CORRECTION

PATENT NO.    : 6,415,170 B1
DATED         : July 2, 2002
INVENTOR(S)   : Loutis, Nicolaus It is certified that error appears in the above-identified patent and that said Letters Patent is hereby corrected as shown below:

Column 7,
Line 64, delete "portionwise" and insert in place thereof -- portion wise --.
Line 66, delete "stirred." and insert in place thereof -- stirred, --.

Column 10,
Line 40, insert -- A -- preceding "biomedical".

Signed and Sealed this

Twenty-ninth Day of April, 2003

JAMES E. ROGAN
*Director of the United States Patent and Trademark Office*